US012661319B2

(12) United States Patent
Picone et al.

(10) Patent No.: US 12,661,319 B2
(45) Date of Patent: Jun. 23, 2026

(54) MYELIN NANOVESICLES AND USES THEREOF

(71) Applicant: Consiglio Nazionale Delle Ricerche, Rome (IT)

(72) Inventors: Pasquale Picone, Carini (IT); Domenico Nuzzo, Alcamo (IT); Fabio Salvatore Palumbo, Termini Imerese (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 729 days.

(21) Appl. No.: 17/925,262

(22) PCT Filed: May 12, 2021

(86) PCT No.: PCT/IB2021/054046
§ 371 (c)(1),
(2) Date: Nov. 14, 2022

(87) PCT Pub. No.: WO2021/229461
PCT Pub. Date: Nov. 18, 2021

(65) Prior Publication Data
US 2023/0346703 A1     Nov. 2, 2023

(30) Foreign Application Priority Data

May 13, 2020     (IT) ........................ 102020000010888

(51) Int. Cl.
*A61K 9/1275*     (2025.01)
*A61K 9/1277*     (2025.01)
*A61K 49/00*     (2006.01)

(52) U.S. Cl.
CPC .......... *A61K 9/1275* (2013.01); *A61K 9/1277* (2013.01); *A61K 49/008* (2013.01)

(58) Field of Classification Search
None
See application file for complete search history.

(56) References Cited

U.S. PATENT DOCUMENTS 5,849,886 A * 12/1998 Maatta ............... C07K 14/4713
530/839
2019/0365656 A1* 12/2019 Getts .................. C07K 14/4713

FOREIGN PATENT DOCUMENTS

WO     WO2017/120222 A1     7/2017

OTHER PUBLICATIONS

Poser et al (Journal of the Neurological Sciences, 79(1), 83-90, 1987). (Year: 1987).*
Inaki Osorio-Querejeta et al: "Therapeutic Potential of Extracellular Vesicles for Demyelinating Diseases; Challenges and Opportunities", Frontiers in Molecular Neuroscience, vol. 11, Nov. 23, 2018.
Hurwitz Stephanie N. et al: "Extraction of Extracellular Vesicles from Whole Tissue", Journal of Visualized Experiments, No. 144, Mar. 26, 2020, pp. 1-16.
Alessi A Farinazzo et al: "Nanovesicles from adipose-derived mesenchymal stem cells inhibit T lymphocyte trafficking and ameliorate chronic experimental autoimmune encephalomyelitis", Scientific Reports, vol. 8, No. 1, May 10, 2018, pp. 1-11.
Carlo Petrini: "Ethical and legal considerations regarding the ownership and commercial use of human biological materials and their derivatives", Journal of Blood Medicine, vol. 3, Sep. 7, 2012, pp. 87-96.
Vella Laura J. et al: "A rigorous method 1-25 to enrich for exosomes from brain tissue", Journal of Extracellular Vesicles, vol. 6, No. 1, Dec. 1, 2017, p. 1348885.
International Search Report and Written Opinion from International Application No. PCT/IB/2021/054046 dated Sep. 13, 2021, 15 pages.

* cited by examiner

*Primary Examiner* — Celeste A Roney
(74) *Attorney, Agent, or Firm* — Fish IP Law, LLP

(57)     ABSTRACT

The invention concerns nanovesicles of nanostructured myelin and uses thereof in the treatment of demyelinating and neurodegenerative diseases of the central (CNS) and peripheral (PNS) nervous system. Under another aspect, processes for the preparation of myelin nanovesicles having particular characteristics that make them suitable for recovery of the myelin sheath, where it is compromised, as a drug delivery system for CNS or PNS, and for immunotolerance, are described.

18 Claims, 6 Drawing Sheets

Myelin

Myelin

MYELIN NANOVESICLES AND USES THEREOF

CROSS REFERENCE TO RELATED APPLICATION(S)

This patent application claims the benefit and priority of PCT application serial no. PCT/IB2021/054046 filed May 12, 2021, which claims priority to Italian application serial no. 102020000010888 filed May 13, 2020, each of the disclosures of which are incorporated by reference herein in their entirety as part of the present application.

DESCRIPTION

Field of the Invention

The invention concerns nanovesicles based on nanostructured myelin extracted from brain tissue and uses thereof in the treatment of demyelinating and neurodegenerative diseases of the central (CNS) and peripheral (PNS) nervous system. Under another aspect, processes for the preparation of nanovesicles based on myelin having characteristics that make them suitable for recovery of the myelin sheath, where it is compromised, as a drug delivery system for CNS or PNS, and for immunotolerance, are described.

State of the Art

Demyelinating diseases form a large group of diseases characterized by an impairment of myelin surrounding nerve cells. Demyelinated axons are susceptible to damage, degeneration, and death resulting in devastating disabilities. Genetics, infectious agents, autoimmune reactions, and other unknown factors can cause demyelinating diseases.

Multiple sclerosis (MS) is a demyelinating and neurodegenerative disease affecting the central nervous system, characterized by an abnormal reaction of immune defenses.

The inflammatory process, triggered by the immune system, can damage myelin (the sheath that surrounds and insulates nerve fibres). This process, called demyelination, can result in areas of myelin loss or injury, which are referred to as plaques. Plaques can evolve from an initial inflammatory phase to a chronic phase, in which they show scar-like characteristics (called sclerosis).

Other demyelinating diseases are acute disseminated encephalomyelitis, adrenoleukodystrophy and adrenomyeloneuropathy, Leber's hereditary optic neuropathy.

The remyelination process involves reconstructing the myelin layer around the damaged axons. There are still no known treatments aimed at promoting the repair of neurons' and nerve fibres' myelin and its reconstitution, thus preventing the consequent neurodegeneration. Recent research in the field of remyelination has mainly focused on reintegration of drugs already approved for other diseases by the Food and Drug Administration and the European Medicine Agency. On the other hand, emerging agents, such as the mAbs opicinumab and GNbAC1, are targeting entirely new and unconventional pathways. Some of them have already been tested in clinical trials in which they have been found to exert beneficial effects on remyelination and neurodegeneration/neuroprotection. [Kremer et al., 2019, Cadavid et al., 2019].

Furthermore, the autoimmune response that leading to myelin destruction, and being responsible for multiple sclerosis, could be strongly contained thanks to a therapy that teaches the immune system to recognize antigens (Ags)

triggering the response (immunotolerance) as "friends". The first step towards this type of treatment is to identify the target antigens, which trigger self-reactive immunity. It is known that antigens in MS can differ among patients and are multiple in the same patient, and specificity of the autoimmune response can shift from one initial myelinated antigenic epitope to another epitope or Ag. This concept of evolution in the antigenic specificity of the pathogenic response is called "epitope spread".

Tolerance studies with myelinated peptides in animal models of MS have shown to be safe and able to induce immunomodulatory responses [Lutterotti A, et al. 2013]. (See also: https://bit.ly/2W3u6H0 e https://bit.ly/2W2kufS). In experimental studies, one of the main proteins of the myelin sheath, the whole myelin basic protein (MBP) or fragments thereof were tested as a therapeutic strategy in MS [Goverman J. M. 2011]. The MBP protein is an extrinsic protein of the myelin membrane and is therefore associated with lipids. MBP is known to undergo, as an intrinsically disordered protein, conformational changes from an extended conformation in aqueous solution into a self-assembled protein with elements of secondary ordered structure caused by interaction with lipids. Furthermore, the MBP family includes numerous isoforms and undergoes a complex series of post-translational modifications, resulting in charge isomers designated as C1 to C8 components. An important post-translational modification of MBP is deimination, the enzymatic conversion of arginine into citrulline by peptidylarginine deiminase. De-imination reduces the net positive charge of the protein [Doyle and Mamula 2001, 2002]. Therefore, it is known that an important role in the pathology of multiple sclerosis is played not as much by the myelin basic protein (MBP) itself but more by its interaction with the native environment thereof, consisting of lipids of the myelin sheath, or by its different isoforms or post-translational modifications [Doyle and Mamula 2001, 2002].

Adding to the complexity is that antigenic epitopes could be due to post-translational modifications of proteins, interaction of proteins with lipids or be comprised of lipids themselves, or glycolipids that have not yet been identified. Overall, the identity of the relevant Ags in MS remains unknown, and this lack of knowledge about Ag hinders the development of effective treatments for MS.

Recently, due to their ability to overcome the blood brain barrier, vesicles or nanoparticles have been proposed as a valuable tool for the delivery of drugs for diseases involving the central nervous system [Picone et al., 2016 e 2018] and issues related to common therapies [Croese et al., 2018; Casella et al., 2018]. Compared to traditional methods, drug delivery systems have numerous advantages; in fact, they are able to selectively deliver the drug to a specific site, protect it from degradation, control its release, avoid adverse systemic side effects and, if properly designed, cross biological barriers [Picone et al., 2016]. All these advantages allow a reduction in the therapy doses and frequency of administration with greater patient compliance. However, the use of drug-loaded or non-drug-loaded nano-carriers/vesicles suitable for myelin repair is not yet present in the medical landscape.

The object of the present invention is therefore to provide an effective treatment to promote, on the one hand, the repair of neurons and nerve fibres, by means of reconstitution of the myelin sheath, leading to a recovery of lost functions and reduction of the resulting disability. On the other hand, it is to provide an effective treatment for releasing drugs to the CNS and for development of immunotolerance.

SUMMARY OF THE INVENTION

The invention concerns myelin nanovesicles produced starting from myelin extracted from animal brain tissue which has 70-85% by weight of lipids and 15-30% by weight of proteins.

In particular, a nanovesicle is described having a diameter in the range from 30 to 200 nm, a zeta potential in the range from −10 to −50 mV, named nanovesicle and comprising nanostructured myelin, wherein said myelin comprises from 70 to 85% by weight of lipids and from 15 to 30% by weight of proteins.

These nanovesicles produced through specific protocols have a spheroidal morphology and present lipids and proteins typical of the myelin sheath. In fact, in addition to the main proteins of the myelin sheath (myelin basic proteins or BMPs, Myelin proteolipid proteins or PLPs, Myelin oligodendrocyte glycoproteins or MOG, Myelin-associated glycoprotein or MAG, 2'3'-cyclic-nucleotide 3'-phosphodiesterase or CNP), the nanovesicles naturally contain more than 400 proteins present in a lipid structure under native conditions (conformation, isoforms, epitope exposure, and Ag-lipid interaction). Thus, myelin vesicles contain most of, if not all, the relevant myelin antigens. The vesicles by origin (brain tissue), nature (comprised of myelin, i.e. lipids and proteins), preparation (physical processes), physical-chemical characteristics, and biological properties (presence of different myelin antigens in the native conformation, presence of lipids, interaction Antigens-lipids) represent a potential and innovative strategy in the field of demyelinating diseases. The nanovesicles were named MyVes.

Under another aspect, the invention concerns the use of myelin nanovesicles for use as a medicament.

Under yet another aspect, the invention concerns the use of myelin nanovesicles for the treatment of demyelinating diseases.

Under a further aspect, a process for the preparation of myelin nanovesicles is described, having the steps of:

a. preparing a myelin dispersion in water at a concentration between 0.1 mg/ml and 10 mg/ml;

b. homogenizing the myelin dispersion of step a. with an Ultra-Turrax (Ika) at an intensity in the range from 8,000 to 22,000 rpm, for a time in the range from 5 to 15 minutes, to obtain a homogenized solution;

c. sonicating the homogenized solution of step b. with a sonicator (Bandelin) at an intensity of 35-45 kHz for a time in the range from 1 to 15 minutes, to obtain myelin nanovesicles having a diameter in the range from 30 to 200 nm, a zeta potential in the range from −10 to −50 mV and presenting proteins typical of the myelin sheath.

The invention still describes the use in immunotolerance and the use of myelin-based nanovesicles for the treatment of neurodegenerative diseases of the central and peripheral nervous system, wherein said neurodegenerative diseases of the central or peripheral nervous system are Alzheimer's Disease, Parkinson's Disease, Amyotrophic Lateral Sclerosis.

In a further embodiment, a process for the preparation of myelin nanovesicles is described, having the steps of:

a. preparing a myelin dispersion in a polar solvent at a concentration in the range from 0.1 mg/ml to 10 mg/ml;

b. flowing the myelin dispersion of step a. (as the internal phase) through a microfluidic chip for micro-mixing (micro-mixing chip of the split-and-recombine type) (Dolomite, UK), using water as the external phase. The procedure was carried out using an Elveflow microfluidic machine as the flow and pumping control unit and equipped with an OB1 pressure regulator operating at pressures of 2-8 bar and flow sensors operating in the range 0-5,000 μl/min with a precision of 10 μl/min, to obtain myelin nanovesicles having a diameter in the range from 30 to 200 nm, a zeta potential in the range from −10 to −50 mV and presenting proteins typical of the myelin sheath.

The applied pressures pushed the myelin solution into the internal channel and the aqueous phase into the external channel, with a flow range of between 10 and 200 μl/min.

DESCRIPTION OF THE DRAWINGS

The invention will now be described in detail and referring to the attached Figures in which:

FIG. 5B1 shows the presence of two prominent broad bands at 2930 cm$^{-1}$ and 2884 cm$^{-1}$ which can be attributed to the asymmetrical and symmetrical stretching vibrations of the carbon-hydrogen bonds (—CH$_2$ and —CH$_3$) (Nzai et al, 1998; Casal et al., 1984). In FIG. 5B2, the presence of phospholipids is confirmed by the presence of the two main peaks at 1109 cm$^{-1}$ and 1041 cm$^{-1}$ due to the stretching of PO$^{2-}$ groups (FIG. 5B2) (Nzai et al, 1998; Casal et al., 1984).

DETAILED DESCRIPTION OF THE INVENTION

Figure 1:
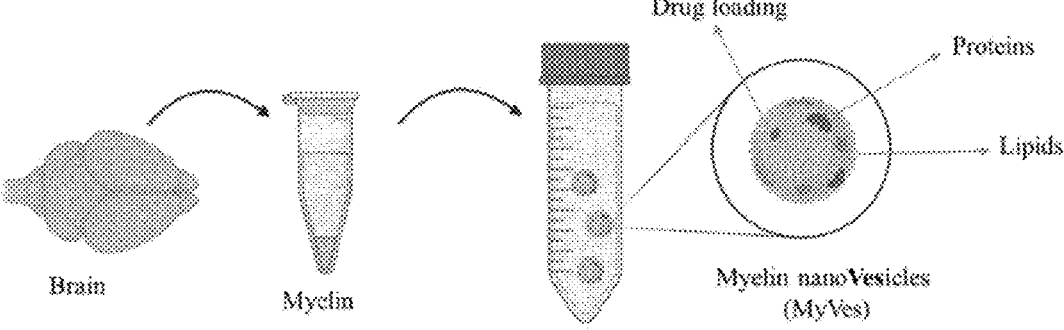
FIG. 1 shows a scheme of the procedure for preparing MyVes myelin vesicles starting from animal (rat, mouse, bovine) brain tissue, from which myelin is extracted, and a representative image of MyVes, i.e. comprised of lipids and proteins. These proteins could potentially be responsible for both anchoring MyVes to the demyelinated axon or damaged myelin itself, and for the immunotolerance effect; furthermore, the possibility of loading MyVes with a drug is depicted.

The invention therefore concerns a nanovesicle having a diameter in the range from 30 to 200 nm, a zeta potential in the range from −10 to −50 mV, said nanovesicle comprising nanostructured myelin, wherein said myelin comprises from 70 to 85% by weight of lipids and from 15 to 30% by weight of proteins.

The invention concerns myelin nanovesicles produced starting from myelin extracted from animal (mouse, rat, bovine) or human brain tissue, having 70-85% of lipids and 15-30% by weight of proteins. These vesicles produced through specific protocols have a spheroidal morphology, an average diameter in the range from 30 to 200 nm, a zeta potential in the range from −10 to −50 mV, wherein said myelin nanovesicles present lipids and proteins typical of the myelin sheath. In fact, myelin nanovesicles naturally contain more than 400 proteins (442), the most representative of which, accounting for 70% of the protein component in the sample, in percentage terms, are Myelin basic protein, (P02688), Myelin proteolipid protein (P60203), Myelin-oligodendrocyte glycoprotein (Q63345), 2'3'-cyclic-nucleotide 3'-phosphodiesterase (P13233), Calmodulin-1 (PODP29), Myelin-associated glycoprotein (P07722), while the remaining 432 proteins account for 30% of the protein amount (relative %<1%).

These proteins are present in a lipid structure under native conditions (conformation, isoforms, epitope exposure, and Ag-lipid interaction). Therefore, myelin vesicles contain most of, if not all, relevant myelin antigens.

The vesicles of the present invention are therefore originated from brain tissue, are produced through physical processes, are comprised of lipids and proteins that interact in a native conformation, have physical-chemical characteristics (size, zeta potential, morphology, and stability) and biological properties (presence of different myelinated antigens in the native conformation, presence of lipids, Antigen-lipid interaction, ability to cross a (BBB) model), which make them suitable for biomedical applications in the field of demyelinating diseases.

WO2017/120222 describes synthetic poly (lactide-co-glycolide) (PLG) particles comprising fusion proteins separated by a linker, not derived from a tissue. Being originated from brain tissue, the nanovesicles of the present invention, unlike the particles described in WO2017/120222, are comprised of myelin with a membrane-like lipid structure and proteins, in a native environment (protein-lipid interaction) which gives them peculiar physico-chemical properties, organization, interactions, exposure of epitopes and different therapeutic potentials. The particular conformation of the nanoparticles of the present invention allows efficacy in replacing damaged myelin, in immunotolerance and in releasing drugs against demyelinating diseases and/or diseases of the central nervous system, thus improving the efficacy and safety of the treatment compared to traditional drug administration.

The nanovesicles of the present invention can present the lipid component with a unilamellar conformation (Bilayer, membrane-like structure) or multilamellar conformation, be full (such as, for example, solid lipid nanoparticles) or empty such as liposomes.

Furthermore, the lipid component and the proteins of the present nanovesicles are present in the native structure and conformation and have not undergone any physical-chemical modifications selected from the group consisting of fusion, enzymatic cutting, binding or addition of spacers or functional groups, cross-linking.

The myelinated vesicles according to the present invention were characterized as described in the Examples; this is a crucial step necessary to fully understand the origin of their behaviour and subsequently translate their benefits in terms of laboratory performance into specific biomedical applications. For this purpose, the zeta potential is an important parameter for measuring the surface charge of the particles, this value was obtained for the myelinated nanovesicles described herein and ranges from −10 to −50 mV. This parameter is strongly related to the MyVes preparation procedure.

In the present invention, when the definition "myelin nanovesicles" or "MyVes" or "myelin-based nanoparticles" is used, it is intended to include the myelinated nanovesicles described herein comprised of lipids (75-80%) and proteins (15-30%), having a zeta potential ranging from −10 to −50 mV, preferably from −20 to −40 mV, more preferably from −35 to −45 mV.

When the definition "nanostructured myelin" is used, it is intended to include a structure on a nanometric scale with properties and characteristics (physical, biological, etc.) significantly different from those of the same material with a larger structure.

In addition to controlling the stability of a colloidal suspension and its tendency to aggregate, the surface charge also plays an important role in modeling the interactions between nanoparticles and environment. Furthermore, for characterising My Ves other parameters will be required, such as polydispersity index (PDI), stability, drug loading capacity, structure-function relationships (ability to cross biological membranes such as the blood brain barrier, ability to interact with proteins present at the target site, ability to release the carried drug).

Demyelinated structures are susceptible to damage, a process leading to neurodegeneration due to the death of neurons, the cells responsible for propagation of nerve stimuli. Effective treatments to promote repair of neurons and nerve fibres, reconstitution of the myelin sheath, recovery of lost function and reduction of the resulting disability are not yet available. Nanotechnology is a promising new approach that has made a huge contribution in the diagnosis and treatment of CNS-related disorders. However, the use of vesicles, or nano-carriers in general, manufactured with myelin and loaded with drugs, is not yet present in the medical landscape. The myelin nanovesicles according to the present invention are a valuable and effective tool to replace damaged myelin, as a drug delivery system against demyelinating diseases of the nervous system, and as an immunotolerance system.

In a preferred embodiment, the myelin nanovesicle according to the present invention has a diameter in the range from 30 to 200 nm, preferably from 90 to 110 nm.

In a more preferred embodiment, the myelin nanovesicle according to the present invention has a zeta potential in the range from −10 to −50 mV and present a lipid and protein component. The proteins are myelin basic proteins (BMPs), myelin proteolipid proteins (PLPs) and myelin oligodendrocyte glycoproteins (MOG) and more than 400 other lipid associated proteins.

The myelin nanovesicles according to the present invention can be loaded with a compound or a molecule, preferably said compound is a drug, a contrast agent, a fluorescent probe, cytokines, growth factors, antioxidants, anti-inflammatories, immunomodulators, or any other molecule active in favouring or assisting the treatment of sclerosis, myelin regeneration and neurodegenerative diseases of the CNS and PNS. The nanovesicles can vehiculate drugs and biomolecules with a therapeutic effect (drug delivery) to the central and peripheral nervous system.

Under another aspect, the invention concerns the use of myelin nanovesicles for use as a medicament.

Under yet another aspect, the invention concerns the use of myelin nanovesicles for the treatment of demyelinating diseases. In a preferred embodiment, these demyelinating diseases are multiple sclerosis (MS), acute disseminated encephalomyelitis, adrenoleukodystrophy, adrenomyeloneuropathy, and Leber's hereditary optic neuropathy.

The invention therefore describes the use of myelin-based nanovesicles for the treatment of neurodegenerative diseases.

MyVes could be a valuable and effective tool to replace damaged myelin and as a drug delivery system against demyelinating diseases and/or central nervous system diseases. MyVes, could improve the drug release profile at the target site, stability, absorption and biodistribution, thus improving the efficacy and safety of treatment compared to traditional drug administration.

Under yet another aspect, the use of myelin nanoparticles for the repair of damaged myelin at the level of the axons of the central and peripheral nervous system is described.

Therefore, myelin nanovesicles may be relevant for several aspects including myelin repair and delivery of drugs to the target site of the CNS and PNS.

Furthermore, since MS is an autoimmune disease, strategies for tolerance of specific antigens are used for therapeutic purposes. Peptides (442) present singly or synergistically in MyVes may be able to induce immunotolerant responses, and their use in immunotolerance is described. In fact, myelin vesicles contain most of, if not all, the relevant myelinated Ags, in a natural lipid environment (Ags-lipid interaction), therefore they have the potential to induce Ag-specific tolerance and suppress the disease driven by an immune response against myelinated Ags. The use of our myelin vesicles would circumvent the need to identify relevant myelin Ags in each patient, thus increasing the possibility that myelin vesicles could be a universally applicable Ag-specific MS therapy, as well as being a drug carrier and reconstructing myelin.

The invention still describes the use of myelin-based nanovesicles for the treatment of neurodegenerative diseases of the central and peripheral nervous system, wherein said neurodegenerative diseases of the central or peripheral nervous system are Alzheimer's Disease, Parkinson's Disease, Amyotrophic Lateral Sclerosis.

A further aspect describes a process for the preparation of myelin nanovesicles having the steps of:
  a. preparing a dispersion of myelin in water at a concentration ranging from 0.1 mg/ml to 10 mg/ml;
  b. homogenizing the myelin dispersion of step a. with an Ultra-Turrax (Ika) at an intensity in the range from 8,000 to 22,000 rpm, for a time in the range from 1 to 15 minutes, to obtain a homogenized dispersion;
  c. sonicating the homogenized dispersion of step b. with a sonicator (Bandelin) at an intensity in the range from 35 to 45 kHz for a time from 1 to 15 minutes, to obtain myelin nanovesicles having a diameter in the range from 30 to 200 nm, a zeta potential in the range from −10 to −50 mV and presenting proteins typical of the myelin sheath.

In one preparation embodiment, the dispersion of step a. is prepared by injecting myelin, previously dissolved in a volatile organic solvent miscible with water, into the aqueous medium, during the mixing step of step b.

An example of implementation of this process is described in Example 2 as "Procedure 1".

In one embodiment, a process for the preparation of myelin nanovesicles is described having the steps of:

a. preparing a myelin dispersion in a volatile organic solvent, preferably tert-Butanol at a concentration from 0.1 to 1 mg/ml.

b. injecting the myelin dispersion of step a. in distilled water and homogenizing the myelin dispersion obtained with Ultra-Turrax (Ika) at an intensity in the range from 8,000 to 22,000 rpm for a time in the range from 5 to 15 minutes, to obtain a homogenized solution;

c. sonicating the homogenized solution of step b. with a sonicator (Bandelin) at an intensity in the range from 35 to 45 kHz for a time from 1 to 15 minutes, to obtain myelin nanovesicles having a diameter in the range from 30 to 200 nm, a zeta potential in the range in the range from –10 to –50 mV and presenting proteins typical of the myelin sheath.

An example of implementation of this process is described in Example 2 as "Procedure 2".

This process aims to establish a suitable manufacturing procedure for obtaining a passive loading of therapeutic agents (i.e., direct inclusion of the therapeutic agent during self-assembly of myelinated phospholipids), the myelin extract was dissolved in the appropriate volatile organic solvent miscible with water (i.e., tert-butanol, ethanol, isopropanol, tetrahydrofuran, and other water-miscible volatile polar solvents can be used).

Under another aspect, a nanovesicle is described which can be obtained according to the procedure having the steps of:

a. preparing a myelin dispersion in a volatile organic solvent, preferably tert-Butanol, at a concentration from 0.1 to 1 mg/ml.

b. injecting the myelin dispersion of step a. in distilled water and homogenizing the myelin dispersion obtained with Ultra-Turrax (Ika) at an intensity in the range from 8,000 to 22,000 rpm for a time in the range from 5 to 15 minutes, to obtain a homogenized solution;

c. sonicating the homogenized solution of step b. with a sonicator (Bandelin) at an intensity in the range from 35 to 45 kHz for a time from 1 to 15 minutes, to obtain myelin nanovesicles having a diameter in the range from 30 to 200 nm, a zeta potential in the range from –10 to –50 mV and presenting typical myelin sheath proteins; wherein said nanovesicle has a diameter in the range from 30 to 200 nm, a zeta potential in the range from –10 to –50 mV, said nanovesicle comprising myelin, wherein said myelin comprises from 70 to 85% by weight of lipids and from 15 to 30% by weight of proteins.

In a further embodiment, a process is described for the preparation of myelin nanovesicles having the steps of:

a. preparing a myelin solution in tert-Butanol (or a suitable volatile polar solvent) at a concentration in the range from 0.1 to 1 mg/ml;

b. flowing the myelin solution of step a. as an internal phase, and distilled water as an external phase, through a microfluidic chip for micro-mixing of the "split-and-recombine" type from Dolomite, UK, using an "Elveflow" microfluidic machine equipped with OB1 pressure regulator operating at pressures of 2-8 bar, and flow sensors operating in the range 0-5,000 μl/min with an accuracy of 10 μl/min, as a flow and pumping control unit. The applied pressures pushed the myelin solution into the internal channel and the aqueous phase into the external channel, with a flow range between 10 and 200 μl/min, to obtain myelin nanovesicles having a diameter in the range from 30 to 200 nm, a zeta potential in the range from –10 to –50 mV and presenting proteins typical of the myelin sheath.

An example of implementation of this process is described in Example 2 as "Procedure 3".

In a preferred embodiment, the process of the invention (Process 1, 2 or 3) has the additional step of freeze-drying the myelin nanoparticles obtained by lyophilization, in order to obtain lyophilized myelin nanoparticles.

Stability tests were carried out to evaluate the shelf-life of MyVes, following incubation of the sample at room temperature for a period of one month, and the results show excellent stability for MyVes.

Through the use of cellular or animal models, the ability of My Ves to interact with neuronal cells and their subcellular localization is analysed.

Under still another aspect, nanovesicles obtainable according to any process of the present invention (Process 1, 2 or 3) are described, said nanovesicles having a diameter in the range from 30 to 200 nm, a zeta potential in the range from –10 to –50 mV, and comprising myelin, wherein said myelin comprises from 70 to 85% by weight of lipids and from 15 to 30% by weight of proteins.

Preferably the proteins comprise Myelin basic protein (P02688), Myelin proteolipid protein (P60203), Myelin-oligodendrocyte glycoprotein (Q63345), 2'3'-cyclic-nucleotide 3'-phosphodiesterase (P13233), Calmodulin-1 (PODP29), Myelin-associated glycoprotein (P07722), and myelin is nanostructured. These proteins are present in the structure and native conformation associated with lipids, where they can interact synergistically (protein-protein, protein-lipid interaction) thus enhancing the effect of the produced nanovesicle.

More preferably, the nanovesicles have a diameter in the range from 90 to 110 nm and a zeta potential in the range from –35 to –45 mV.

Figure 2:
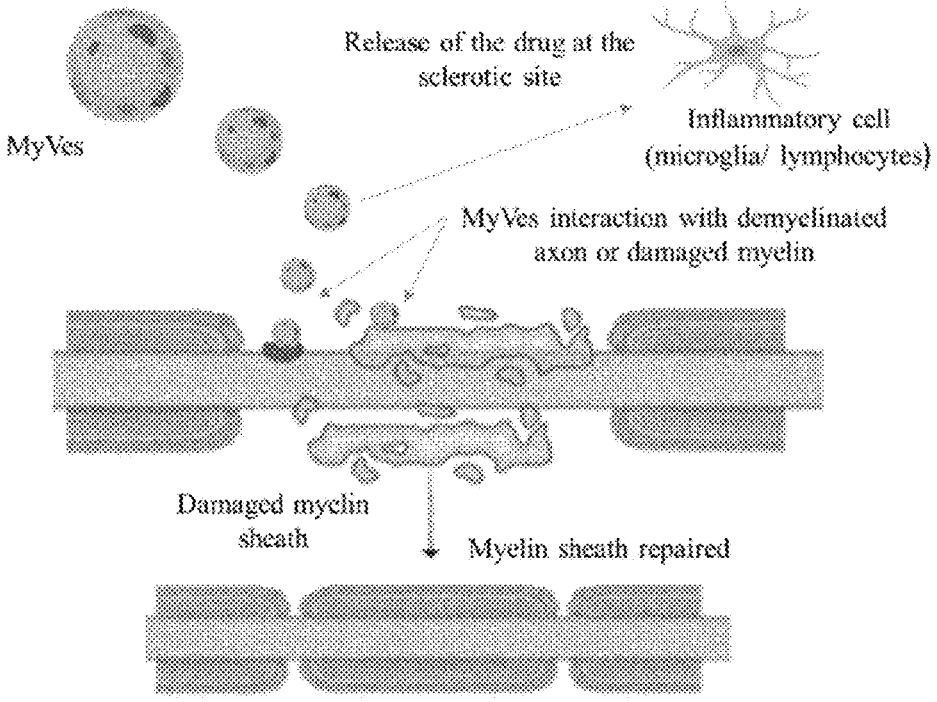
FIG. 2 shows a scheme of the myelin repair process through the possible interaction of proteins present in MyVes with proteins exposed by the demyelinated neuron or by the damaged myelin itself; as well as the release of the drug in the demyelinated active site and in immune cells, such as microglia or reactive lymphocytes.

FIG. 1 shows a simplified scheme of the procedure for preparing MyVes myelin vesicles, and a representative image of the MyVes, i.e. comprised of lipids and proteins, the possibility of loading the MyVes with a drug is also represented. Without being bound to a particular theory, the proteins present in MyVes (442), identified by a proteomic approach, could be involved either in recognition sites present on the surfaces of demyelinated neurons or in damaged myelin, thus allowing the anchoring of the new myelin layer and its subsequent reconstruction (FIG. 2), or in immunotolerance. The ability of MyVes to load and release drugs, to repair damaged myelin and the immunotolerance activity will be evaluated using specific in vitro and in vivo assays.

Examples of embodiments of the present invention are provided below for illustrative purposes.

EXAMPLES

Example 1: Myelin Isolation

Isolation from Rat Brain:

Once explanted, the rat brain was placed on ice and was pulverized by means of a mortar and the use of nitrogen. Subsequently, about 60 mg were collected and homogenized in a homogenizer with 180 μl of 0.32 M Sucrose solution, 10% protease inhibitors (Amersham Biosciences, Milan, Italy) and 10% phosphatase inhibitors (Cocktail II and III; Sigma-Aldrich, Milan, Italy). The homogenate was placed in an ultracentrifuge tube where 720 μl of a 2 M sucrose solution and 300 μl of a 0.1 mM $CaCl_2$) solution were added.

Figure 3A:
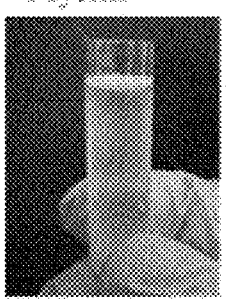
FIG. 3A shows a test tube with rat or bovine brain myelin isolated and obtained by centrifugation of the brain homogenate using a sucrose gradient.
Figure 3B:
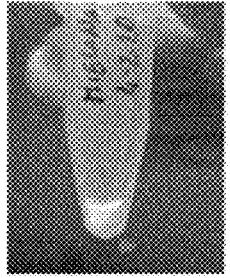
FIG. 3B shows a test tube with myelin extracted and washed with water in order to eliminate sucrose, and then centrifuged (5,000 rpm for 15 minutes) to remove the washing water, freeze-dried and frozen.

Subsequently, 1.8 ml of a 1 M sucrose solution were carefully superimposed on this solution, and the whole was centrifuged at 127,000 RCF for 3 h at 4° C. [Franklin et al., 2016]. After ultracentrifugation, the myelin that was on the surface of the tube was collected (FIG. 3A). The collected myelin was placed in a 15 ml tube and 3 washings were carried out in distilled water (10 ml) by centrifugation at 5,000 rpm for 15 minutes. At the end of this procedure, myelin was freeze-dried to obtain it in the form of a powder (FIG. 3B).

Myelin isolation can also be performed from bovine brain tissue.

In fact, since the myelin sheath is a structure surrounding the axons of vertebrate neurons and having a highly conserved composition and structure, this protocol could also be applied to a bovine.

The rat brains were from the ATeN Center—Stabulario con sale operatorie per piccoli animali—in Palermo and were donated in accordance with permit number 69636.N.JCO approved by the Italian Ministry of Health. Compliance with the regulations on animal testing is declared.

Example 2: Preparation of Myelin Vesicles

Procedure 1. Direct Dispersion of the Myelin Extract Under High Energy Mixing

The dried myelin extract was suspended in aqueous medium at a concentration of 0.1 mg/ml and homogenized for 30 minutes with Ultra-Turrax (Ika) at 18,000 rpm and then sonicated for 10 minutes at 35 kHz. After production, the aqueous dispersion was freeze-dried and stored. After dispersion in water, the size of the nanovesicles was found to be equal to 130±60 nm; z potential −7 mV.

Procedure 2. High Energy Nanoprecipitation Procedure

In order to establish a suitable manufacturing procedure for obtaining a passive loading of therapeutic agents (i.e. direct inclusion of the therapeutic agent during self-assembly of myelinated phospholipids), the myelin extract was dissolved in the appropriate organic solvent miscible with water (tert-butanol) at a concentration of 0.1 mg/ml. The solution was slowly added to an aqueous medium by mixing using a high energy procedure with Ultra-Turrax (Ika) at 18,000 rpm and then sonicating for 10 min at 35 KHz. After dispersion in water, the size of the nanovesicles was found to be equal to 100±25 nm, with a z potential equal to −42 mV.

Procedure 3. Controlled Nanoprecipitation by Microfluidic Mixing (Low Energy Procedure)

A low-energy procedure was employed with the aim of avoiding the possible inactivation of protein components of the myelin extract and allowing the encapsulation of therapeutic agents that are unstable towards high-energy manufacturing procedures. The microfluidics procedure allows to control the distribution of the final nanoparticle sizes. In particular, the myelin extract was dissolved in the appropriate volatile organic solvent miscible with water (tert-butanol) at a concentration of 0.1 mg/ml. The solution was flowed through a microfluidic chip for micro-mixing of the split-and-recombine type (Dolomite, UK) using water as the external phase. The procedure was carried out using an Elveflow microfluidic machine as the flow and pumping control unit, equipped with an OB1 pressure regulator operating at pressures of 2-8 bar and flow sensors operating in the range 0-5,000 μl/min with an accuracy of 10 μl/min. The applied pressures pushed the myelin solution into the internal channel and the aqueous phase into the external channel, at 100 μl/min and 200 μl/min, respectively. After production, the aqueous suspension was freeze-dried and stored. The lyophilisate was dispersed in water and produced nanovesicles of 60±10 nm with a z potential equal to −38 mv).

The three procedures for preparing the nanovesicles by means of myelin extraction, formation and characterization of the vesicles were successfully repeated several times, indicating excellent reproducibility of the results obtained.

In addition, stability tests on MyVes, following incubation of the sample at room temperature for a period of one month, showing an excellent stability of the MyVes.

Example 3: Characterization of Myelin Nanovesicles

Figure 4:
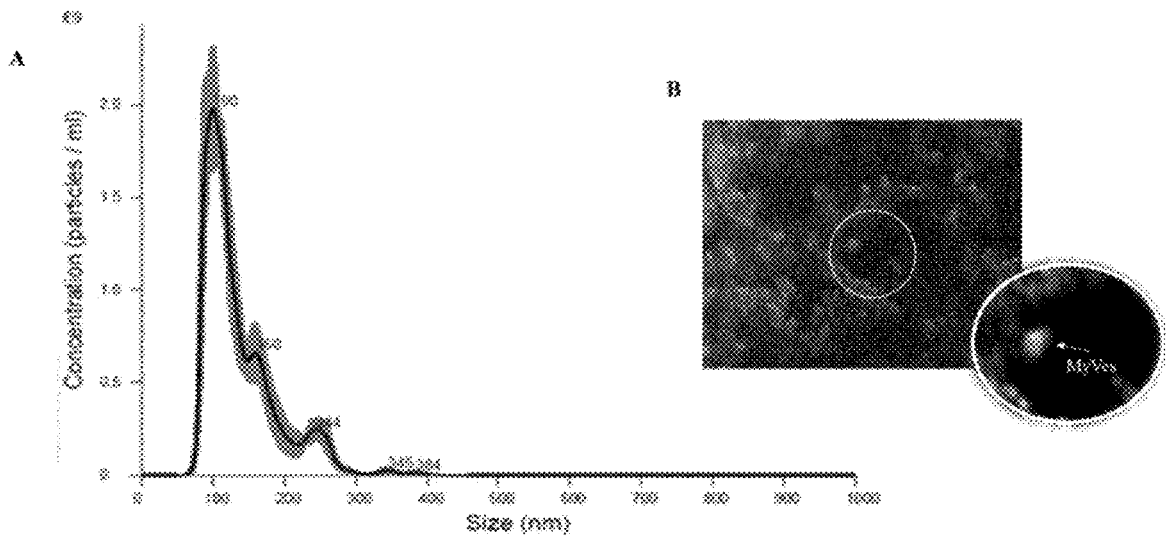
FIG. 4A shows the graph of the size distribution of nanovesicles according to the present invention, measured by Nanoparticle Tracking Analysis (NTA)
FIG. 4B a photograph of MyVes obtained by scanning electron microscopy (SEM).
Figure 5:
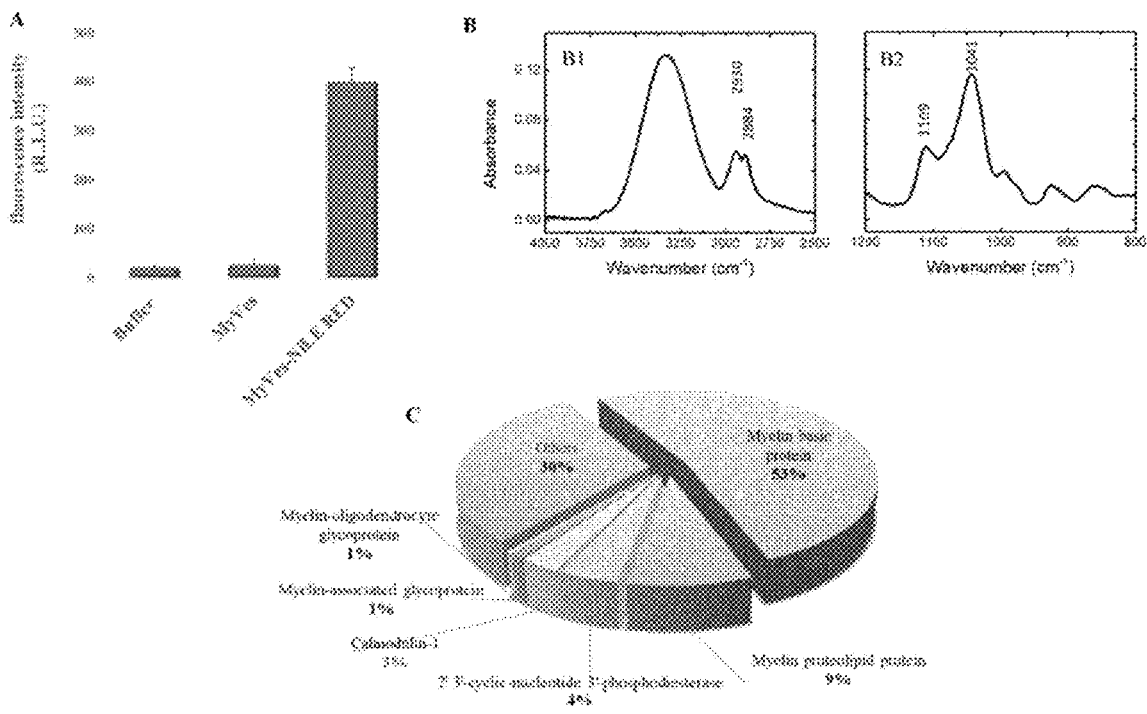
FIG. 5A shows a graph related to the intensity of fluorescence emitted following the interaction of the vesicles with NileRed, a lipophilic dye that emits fluorescence following interaction with lipids. This indicates the lipid nature of the vesicles produced.
FIG. 5B shows the graphs of the ATR-FTIR analysis results which confirm the lipid nature. Specifically, two different regions of the FTIR spectrum: 4000-2500 cm$^{-1}$ (FIG. 5B1) and 1200-800 cm$^{-1}$ (FIG. 5B2), where the bands related to the main functional groups, such as —COOH, —NH, —OH and —CH are present, were analysed. The most intense absorption in the 4000-2500 cm$^{-1}$ region is due to the different-OH stretching vibrations of water molecules which indicate the presence of residual water trapped in the vesicles.
FIG. 5C shows a pie chart showing, expressed in percentage terms, the proteins comprising the 70% of the protein component in the sample, while the remaining 432 proteins comprise only 30% of the protein amount (relative percentage <1% per protein).

The nanovesicles according to the present invention were characterized as reported below. Our preliminary experiments indicate that myelin extraction also carries proteins bound to the myelin sheath, about 15-30% by weight of proteins and the remaining 70-85% of lipids. MyVes nanovesicles produced have a lipid (FIG. 5A, B) and protein nature (FIG. 5C); they were characterized in terms of physical properties with an average size of about 100 nm (FIG. 4), spheroidal morphology by SEM analysis (FIG. 4) and potential between −10 and −50 mV.

Biological Characterization

Figure 7:
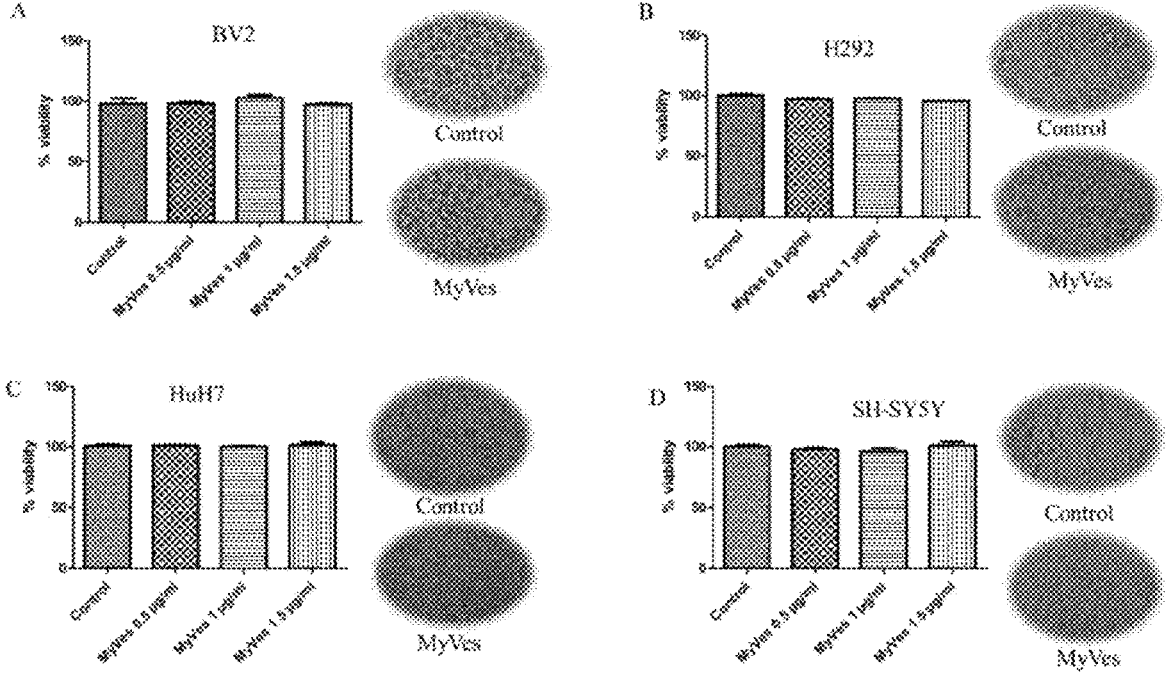
FIGS. 7A-D show the histograms related to the percentage of cell viability and cell morphology following the treatment of different cell lines: neuronal (SH-SY5Y), microglia (BV2), epithelial (H292) and hepatocyte (HuH7) cells in culture with myelin nanovesicles according to the present invention, administered at different doses and times in order to determine their cyto-compatibility.

The My Ves produced were administered at different doses in neuronal (SH-SY5Y), microglia (BV2), epithelial (H292) and hepatocyte (HuH7) cells in order to determine their cyto-compatibility. For this purpose, cells were plated in a 96 multiwell plate at a concentration of 600,000/mL and placed in an incubator with 5% $CO_2$ at 37° C. RPMI or DMEM media (supplemented with 10% Fetal Bovine Serum (FBS), 1% glutamine, 1% antibiotics (penicillin and streptomycin) were used for cell growth and treatments. 24 h after seeding, the myelin vesicles were administered at different doses to the cells over 48 hours. At the end of the treatment, the MTS cell viability test (Promega) was performed. The preliminary results obtained indicate that MyVes are cyto-compatible at the doses and times used (FIG. 7). FIG. 7 shows histograms related to cell viability percentage following the treatment and cell morphologies.

Figure 6:
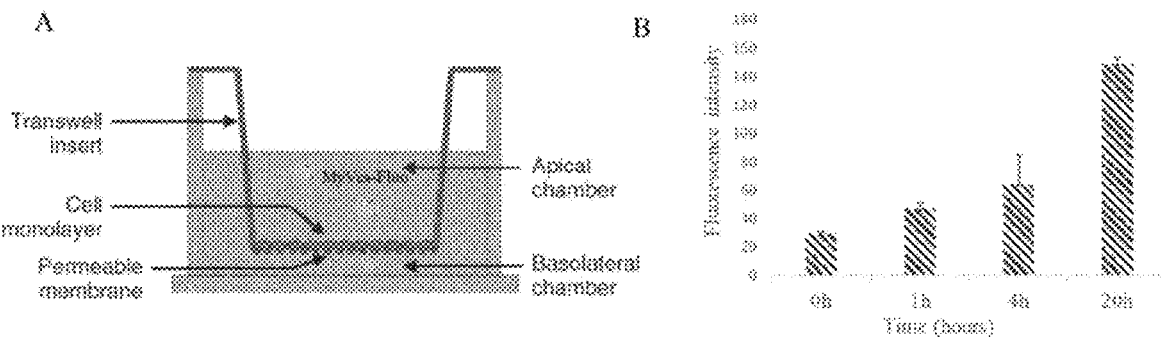
FIG. 6A shows the scheme of an in vitro cellular model of the blood brain barrier (BBB) and the ability of vesicles to cross this system.
FIG. 6B shows the histogram related to the fluorescence measured in the basal chamber, at different times, following the crossing of the myelin vesicles marked with a fluorophore (Alex488) (MyVes-Fluo) in a model of (BBB).

The My Ves produced were labelled with the fluorescent molecule Alex488 (My Ves-Fluo), and their ability to cross this system was verified by means of an in vitro blood brain barrier (BBB) cell model (FIG. 6).

Figure 8:
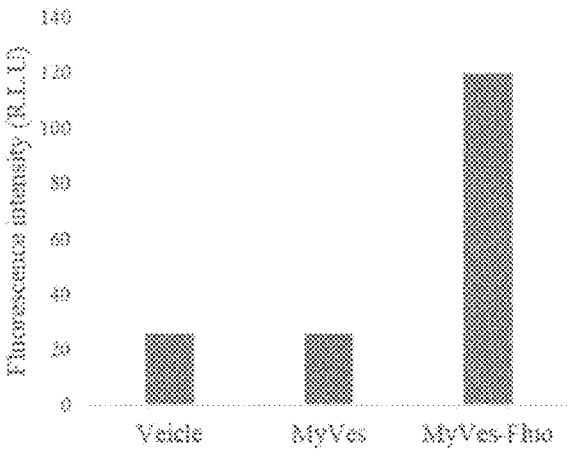
FIG. 8 shows the histogram of fluorescence intensity emitted by MyVes after interaction with the fluorescent probe Di-8-ANEPPS (MyVes-Fluo) compared to MyVes without a probe (MyVes) and the solvent used (vehicle). Such a probe is weakly fluorescent in aqueous media and becomes highly fluorescent when it binds to lipophilic environments such as membranes. This indicates the ability of MyVes to load a molecule/drug.

Furthermore, MyVes were incubated for 30 minutes with the Di-8-ANEPPS fluorescent probe, this probe is weakly fluorescent in aqueous solutions and becomes strongly fluorescent after binding to lipophilic environments, such as biological membranes. Fluorescence analysis by fluorometer (Glomax), showed that MyVes can be loaded with the fluorescent molecule Di-8-ANEPPS, thus indicating that they can be loaded with a molecule/drug. (FIG. 8).

Figure 9:
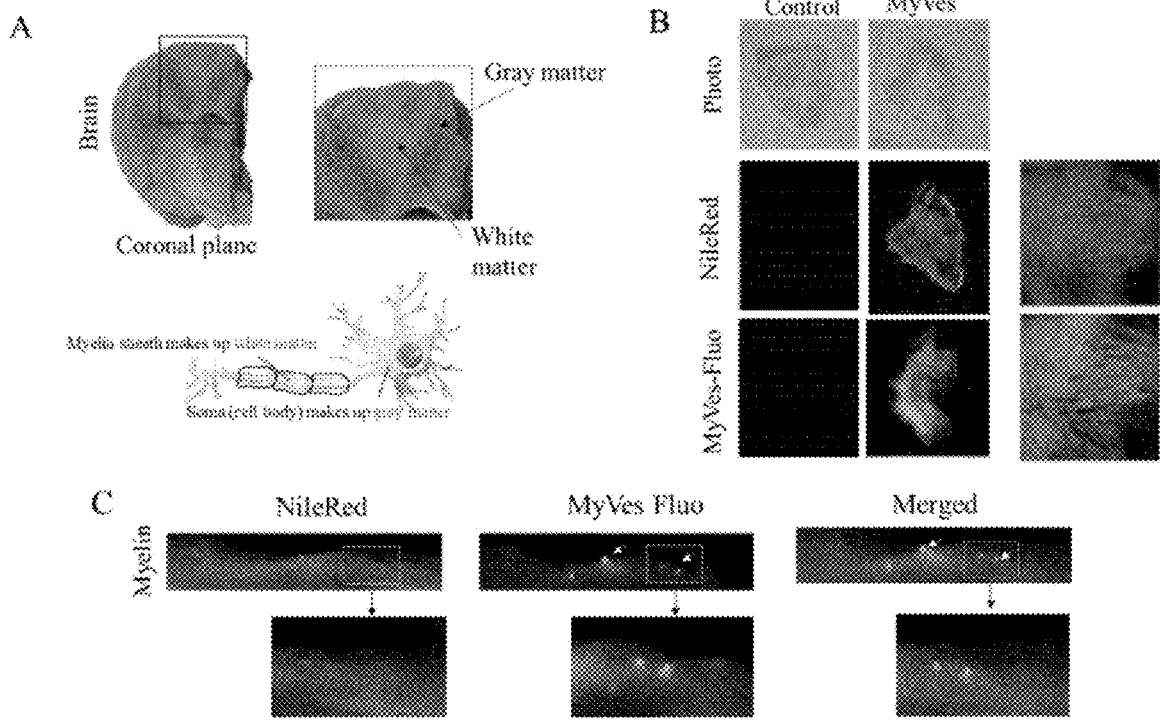
FIG. 9A shows the sagittal section of the mammalian brain which is made of an outer layer of grey matter, consisting of cell bodies, dendrites and unmyelinated axons, and an inner core of white matter, consisting mainly of myelinated axons (depicted in the bottom part).
FIG. 9B shows photographic images of 400-500 μm thick brain sections that were incubated with My Ves labelled with Alex488 (My Ves-Alex488, "MyVes-Fluo") to try and understand the possible affinity of MyVes with grey or white matter. The myelin sheath in the brain slices was labelled with NileRed fluorescent dye ("NileRed"). By visualization with a fluorescence scanner, My Ves-Alex488 ("MyVes-Fluo") was located in the same region as the NileRed, thus indicating the ability of MyVes to interact with the myelin sheath in the white matter.
In FIG. 9C, the interaction of MyVes with myelin fibres, which was visualized by fluorescence microscopy, can be seen.

Subsequently, in order to understand whether the isolated vesicles are able to interact with the myelinated fibres (white matter), the My Ves-Fluo were incubated with brain sections (400-500 μm) where the myelinated fibres had previously been labelled with NileRed (FIG. 9).

Figure 10:
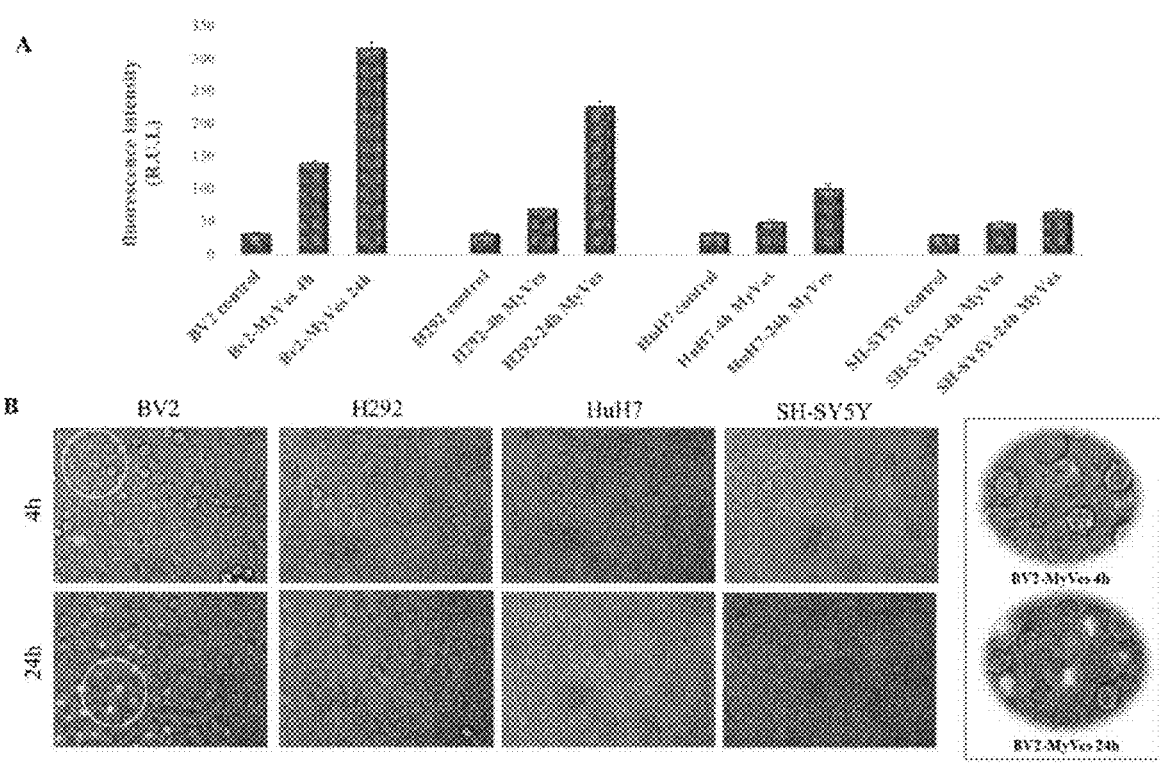
FIG. 10A shows the histogram of the intensity of fluorescence emitted by neuronal (SH-SY5Y), microglia (BV2), epithelial (H292), and hepatocyte (HuH7) cells after treatment with MyVes labelled with an Alex488 fluorescent probe.
FIG. 10B shows the presence and localization of fluorescence emitted by neuronal (SH-SY5Y), microglia (BV2), epithelial (H292), and hepatocyte (HuH7) cells by fluorescence microscopy, after treatment of the cells with MyVes labelled with a Alex488 fluorescent probe, after 4 and 24 hours of treatment. The circular figures refer to the enlargements. This indicates the ability of MyVes to deliver a molecule/drug into a cell, particularly in microglia.

Finally, to understand whether the isolated vesicles are able to interact with the cells, MyVes-Fluo were administered to neuronal (SH-SY5Y), microglia (BV2), epithelial (H292) and hepatocyte (HuH7) cells. The cells, plated in a 96 multiwell plate at a concentration of 600,000/mL, were then incubated with different amounts of labelled MyVes for 4 and 24 hours. From fluorimetric analysis on treated cells, using a fluorimeter (Glomax) after 4 and 24 hours, an increase in fluorescence was detected in a dose-dependent manner compared to the control (untreated cells) (FIG. 10A). In addition, the interaction of MyVes was verified by analysis under a fluorescence microscope (Zeiss) mainly with microglial cells in culture at 4 and 24 hours after treatment (FIG. 10B).

From the detailed description and the Examples reported above, the advantages achieved by means of the myelin nanovesicles and the processes for preparing them, according to the present invention, are apparent. These processes can be conveniently performed in any type of laboratory.

BIBLIOGRAPHIC REFERENCES

Kremer D, Göttle P, Flores-Rivera J, Hartung H P, Küry P. Curr Opin Neurol. 2019 June; 32 (3): 378-384.
Cadavid D, Mellion M, Hupperts R, Edwards K R, Peter A Calabresi, Drulović J, Giovannoni G, Hartung H-P, Arnold D L, Fisher E, Rudick R, Mi S, Chai Y, Li J, Zhang Y, Cheng W, Xu L, Zhu B, Green S M, Chang I, Deykin A, Sheikh S I, on behalf of the SYNERGY study investigators (including Grimaldi L). Lancet Neurol. 2019 Jul. 5.
Lutterotti A, et al. Antigen-specific tolerance by autologous myelin peptide coupled cells: A phase 1 trial in multiple sclerosis. 2013 Sci Transl Med 5: 188ra75.
Goverman J. M. Immune Tolerance in Multiple Sclerosis. Immunol Rev. 2011 May; 241 (1): 228-240.
Doyle, H. A. and Mamula, M. J. 2001. Post-translational protein modifications in antigen recognition and autoimmunity. Trends Immunol. 22:443-449.
Doyle, H. A. and Mamula, M. J. 2002. Post-translational protein modifications: New flavors in the menu of autoantigens. Curr. Opin. Rheumatol. 14:244-249.
Picone P, Ditta L A, Sabatino M A, Militello V, San Biagio P L, Di Giacinto M L, Cristaldi L, Nuzzo D, Dispenza C, Giacomazza D, Di Carlo M. Biomaterials. 2016 February; 80:179-194.
Picone P, Sabatino M A, Ditta L A, Amato A, San Biagio P L, Mule F, Giacomazza D, Dispenza C, Di Carlo M. J Control Release. 2018 Jan. 28; 270:23-36.
Nzai J. M. and Proctor A. Determination of phospholipids in vegetable oil by Fourier transform infrared spectroscopy. Journal of the American Oil Chemists' Society 75 (10): 1281-1289
Casal H. L. and Mantsch H. H. Polymorphic phase Behaviour of phospholipid membranes studied by infrared spectroscopy. Biochimica et Biophysica Acta, 779 (1984) 381-401
Croese T, Furlan R. Mol Aspects Med. 2018 April; 60:52-61. Casella G, Colombo F, Finardi A, Descamps H, Ill-Raga G, Spinelli A, Podini P, Bastoni M, Martino G, Muzio L, Furlan R. Mol Ther. 2018 Sep. 5; 26 (9): 2107-2118.

What is claimed is:

1. A nanovesicle having a diameter in the range from 30 to 200 nm and a zeta potential in the range from −10 to −50 mV, said nanovesicle comprising nanostructured myelin, wherein said nanostructured myelin comprises from 70% to 85% by weight of lipids and from 15% to 30% by weight of proteins, and wherein said myelin is extracted from brain tissue.

2. The nanovesicle according to claim 1, wherein said proteins comprise Myelin basic protein, Myelin proteolipid protein, Myelin-oligodendrocyte glycoprotein, 2'3'-cyclic-nucleotide 3'-phosphodiesterase, Calmodulin-1, and Myelin-associated glycoprotein, wherein said lipids and said proteins are present in the native structure and conformation and have not undergone any physico-chemical modifications selected from the group consisting of fusion, enzymatic cutting, bonding or addition of spacers or functional groups, cross-linking.

3. The nanovesicle according to claim 1, loaded with a substance or a molecule.

4. The nanovesicle according to claim 3, wherein said substance is a drug, a contrast agent, a fluorescent probe, a cytokine, growth factors, antioxidants, anti-inflammatoires, immunomodulators.

5. A method for using a nanovesicle according to claim 1, as a vehicle for vehiculating drugs and therapeutically active biomolecules to the central and peripheral nervous systems.

6. A method for treating demyelinating diseases in a subject in need thereof, said method comprising the step of using the nanovesicle according to claim 1.

7. The method according to claim 6, wherein said demyelinating diseases are multiple sclerosis, acute disseminated encephalomyelitis, adrenoleukodystrophy and adrenomyeloneuropathy, and Leber's hereditary optic neuropathy.

8. A method for treating immunotolerance in a subject in need thereof, said method comprising the step of using the nanovesicle according claim 1.

9. A method for treating a neurodegenerative disease of the central and peripheral nervous system in a subject in need thereof, said method comprising the step of using the nanovesicle according to claim 1.

10. The method according to claim 9, wherein said neurodegenerative diseases of the central and peripheral nervous system are Alzheimer's disease, Parkinson's disease, Amyotrophic Lateral Sclerosis.

11. A process for the preparation of nanovesicles having the steps of:
  a. preparing a myelin dispersion in an aqueous solvent at a concentration in the range from 0.1 mg/ml to 10 mg/ml, wherein said myelin is extracted from brain tissue;
  b. homogenizing the myelin dispersion of step a. with an Ultra-Turrax at an intensity in the range from 8,000 to 22,000 rpm, for a time in the range from 5 to 15 minutes, to obtain a homogenized dispersion;
  c. sonicating the homogenized dispersion of step b. with a sonicator at an intensity of 35-45 kHz for a time of 1-15 minutes, to obtain myelin nanovesicles having a diameter in the range from 30 to 200 nm, and a zeta potential in the range from −10 to −50 mV.

12. The process according to claim 11, wherein the myelin dispersion of step a. is prepared by injecting myelin, previously dissolved in an organic solvent miscible with water, in the aqueous medium, during step b.

13. A process for the preparation of myelin nanovesicles having the steps of:
  a. preparing a myelin dispersion in a polar solvent at a concentration in the range from 0.1 mg/ml to 10 mg/ml, wherein said myelin is extracted from brain tissue;
  b. flowing the myelin dispersion of step a. through a microfluidic chip for micro-mixing, with a flow of between 0 and 5,000 μl/min, to obtain myelin nanovesicles having a diameter in the range from 30 to 200 nm, and a zeta potential in the range from −10 to −50 mV.

14. The process according to claim 11, having the additional step of freeze-drying the myelin nanovesicles obtained from step c., to obtain lyophilized myelin nanoparticles.

15. A nanovesicle obtainable by the process according to claim 11, wherein said nanovesicle has a diameter in the range from 30 to 200 nm, or in the range from 90 to 110 nm, and a zeta potential in the range from −10 to −50 mV, said nanovesicle comprising myelin, wherein said myelin comprises from 70 to 85% by weight of lipids and from 15 to 30% by weight of proteins.

16. The nanovesicle according to claim 15, wherein said proteins comprise Myelin basic protein, Myelin proteolipid protein, Myelin-oligodendrocyte glycoprotein, 2'3'-cyclic-nucleotide 3'-phosphodiesterase, Calmodulin-1 and Myelin-associated glycoprotein.

17. The nanovesicle according to claim 16, wherein said myelin is nanostructured.

18. The nanovesicle according to claim 1, wherein said nanovesicle has a diameter in the range from 90 to 110 nm.

\* \* \* \* \*